US010011852B2

(12) United States Patent
Raoult et al.

(10) Patent No.: US 10,011,852 B2
(45) Date of Patent: Jul. 3, 2018

(54) METHOD FOR PRODUCING METHANE BY MEANS OF AEROBIC CO-CULTURE OF ANAEROBIC MICRO-ORGANISMS

(71) Applicants: FONDATION MEDITERRANEE INFECTION, Marseilles (FR); UNIVERSITE D'AIX MARSEILLE, Marseilles (FR); CENTRE NATIONAL DE LA RECHERCHE SCIENTIFIQUE (CNRS), Paris (FR); INSERM (INSTITUT NATIONAL DE LA SANTE ET DE LA RECHERCHE MEDICALE), Paris (FR)

(72) Inventors: Didier Raoult, Marseilles (FR); Saber Khelaifia, Marseilles (FR); Michel Drancourt, Marseilles (FR)

(73) Assignees: FONDATION MEDITERRANEE INFECTION, Marseilles (FR); UNIVERSITE D'AIX MARSEILLE, Marseilles (FR); CENTRE NATIONAL DE LA RECHERCHE SCIENTIFIQUE (CNRS), Paris (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 0 days.

(21) Appl. No.: 15/304,926

(22) PCT Filed: Apr. 20, 2015

(86) PCT No.: PCT/FR2015/051067
§ 371 (c)(1),
(2) Date: Oct. 18, 2016

(87) PCT Pub. No.: WO2015/162366
PCT Pub. Date: Oct. 29, 2015

(65) Prior Publication Data
US 2017/0191084 A1   Jul. 6, 2017

(30) Foreign Application Priority Data

Apr. 23, 2014  (FR) ...................... 14 53652
Jun. 20, 2014  (FR) ...................... 14 55745

(51) Int. Cl.
C12P 5/02       (2006.01)
C12R 1/01       (2006.01)
C12N 1/00       (2006.01)
C12P 39/00      (2006.01)

(52) U.S. Cl.
CPC ............ C12P 5/023 (2013.01); C12P 39/00 (2013.01)

(58) Field of Classification Search
None
See application file for complete search history.

(56) References Cited

U.S. PATENT DOCUMENTS 4,883,753 A * 11/1989  Belaich ................... C12P 5/023
                                                      435/167

FOREIGN PATENT DOCUMENTS

| DE | 10 2006 035 213 A1 | 1/2008 |
| FR | 2 537 992 A1 | 6/1984 |
| FR | 2 601 690 A1 | 1/1988 |
| FR | 2 990 954 A1 | 11/2013 |
| GB | 2 107 735 A | 5/1983 |
| WO | 2013/004933 A1 | 1/2013 |
| WO | 2013/110891 A1 | 8/2013 |

OTHER PUBLICATIONS

Iino et al. (Candidatus Methanogranum caenicola: a Novel Methanogen from the Anaerobic Digested Sludge, and Proposal of *Methanomassiliicoccaceae* fam. nov. and *Methanomassiliicoccales* ord. nov., for a Methanogenic Lineage of the Class Thermoplasmata, Microbes Environ. vol. 28, No. 2, 244-250, 2013).*
Sikora et al. Lactic Acid Bacteria in Hydrogen-Producing Consortia: On Purpose or by Coincidence? Lactic Acid Bacteria—R & D for Food, Health and Livestock Purposes, Edited by Marcelino Kongo, ISBN 978-953-51-0955-6, 670 pages, Publisher: InTech, Chapters published Jan. 30, 2013).*
Forman et al. Glutathione: Overview of its protective roles, measurement, and biosynthesis. Mol Aspects Med 2009;30(1-2)1-12.*
Tahmasebi et al. Isolation of indigenous Glutathione producing *Saccharomyces cerevisiae* strains, Iran J Pathol. 2016; 11(4):354-362).*
International Search Report dated Jul. 21, 2015 for Application No. PCT/FR2015/051067.
Espacenet English abstract of DE 10 2006 035 213 A1.
Espacenet English abstract of FR 2 537 992 A1.
Espacenet English abstract of FR 2 601 690 A1.
Espacenet English abstract of FR 2 990 954 A1.
Lee, M. J., et al., "Enhanced bio-energy recovery in a two-stage hydrogen/methane fermentation process", Water Science & Technology, vol. 59, No. 11, Jun. 1, 2009, pp. 2137-2143.
Pimentel, M., et al., "Methanogens in Human Health and Disease", The American Journal of Gastroenterology, vol. 1, No. 1, Jul. 1, 2012, pp. 28-33.
Zhang, S., et al., "Effects of VFAs Concentration on Bio-hydrogen Production with *Clostridium Bifermentans* 3AT-ma", Energy Procedia, vol. 14, Mar. 8, 2012, pp. 518-523.

(Continued)

*Primary Examiner* — Iqbal H Chowdhury
(74) *Attorney, Agent, or Firm* — Ladas & Parry LLP

(57) ABSTRACT

The present invention relates to the biological production of methane (Biogas) by co-culture in an aerobic atmosphere of a methanogenic bacterium and of an anaerobic bacterium capable of producing hydrogen, in a culture medium comprising or being supplemented with carbohydrate compound(s), notably starch and/or sugars, and supplemented with antioxidant compound(s).

17 Claims, No Drawings

(56) References Cited

OTHER PUBLICATIONS

Becker, P. M., et al., "Effects of plant antioxidants and natural vicinal diketones on methane production, studied in vitro with rumen fluid and a polylactate as maintenance substrate", Animal Feed Science and Technology, vol. 170, No. 3, Sep. 21, 2011, pp. 201-208.

Krieg, N. R., et al., "Microaerophily and Oxygen Toxicity", Annual Review of Microbiology, vol. 40, No. 1, Oct. 1, 1986, pp. 107-130.

Lagier, J.C., et al., "Microbial culturomics: paradigm shift in the human gut microbiome study", Clinical Microbiology and Infection, 18, 2012, pp. 1185-1193.

\* cited by examiner

METHOD FOR PRODUCING METHANE BY MEANS OF AEROBIC CO-CULTURE OF ANAEROBIC MICRO-ORGANISMS

The present invention relates to a method for producing methane gas ($CH_4$) by microbial culture under aerobic conditions of anaerobic microorganisms.

Methane produced biologically has been considered until recently as only being produced in an anaerobic way, i.e. without oxygen, and usually in the presence of hydrogen, by anaerobic fermentation of a certain number of organic wastes.

In FR 2 537 992, $CH_4$ gas is produced by fermentation and anaerobic degradation of organic wastes. For this, hydrogen is injected which reacts with the produced $CO_2$ in order to form $CH_4$ and thus reduce the $CO_2$ content in a mixture with $CH_4$. Ten to 5,000 liters of $H_2$ gas per $m^3$ of produced $CH_4$ are required.

In FR 2 601 690, a thermophilic methanogen *Methanococcus thermolitotrophicus* is used with a supply of $H_2/CO_2$, the cultivation being accomplished in a medium essentially containing a source of nitrogen and a source of salts which may be assimilated at 110° C. under anaerobic conditions.

Recent research work, since 2006 (1), have shown that in the sea it was possible to detect methane in an aerobic medium exclusively after enrichment with methylphosphonate, with one or several microorganisms fixing the hydrogen (Karl D M, Beversdorf L, Bjorkman K M, Church M J, Martinez A, DeLong E F. Aerobic production of methane in the sea. Nat Geosci 2008; 1:473-8).

In GB 2,107,735, a fermentation method is described for producing methane gas comprising the co-culture of a *Methanobacterium* strain and of a bacteria *Clostridium bifermentans* under anaerobic conditions under an atmosphere containing hydrogen and carbon dioxide ($CO_2$).

Moreover, natural methane is produced in the intestine under anaerobic conditions under the activity of methanogenic microorganisms. In the digestive tract, the methane is produced under the action of Archae methanogenic microorganisms called in particular *Methanobrevibacter smithii* or *Methanomassiliicoccus luminyensis*, which produce methane from hydrogen molecules ($H_2$) produced by the fermentation of sugars with anaerobic bacteria of the digestive tract, in particular by *Bacteroides*, in particular by *Bacteroides thetaiotaomicron*.

The object of the present invention is to provide a novel biotechnological method for producing methane under aerobic conditions.

The inventors surprisingly discovered that it was possible to allow the cultivation of anaerobic bacteria by associating with the culture medium, an antioxidant compound while maintaining the culture of methanogenic archaea.

More specifically, the inventors observed that the addition of antioxidant compounds in a culture medium under an aerobic atmosphere with an anaerobic bacterium capable of producing hydrogen, also allowed cultivation of a methanogenic archaea, because of the production of hydrogen by said anaerobic bacterium. They were able to measure the production of hydrogen in the presence of said anaerobic bacterium and the production of methane by said archaea, made under aerobic conditions, by the association of two anaerobic microorganisms, notably *Methanobrevibacter smithii* or *Methanomassiliicoccus luminyensis* and *Bacteroides thetaiotaomicron*. Thus, producing co-culture chambers with *Bacteroides thetaiotaomicron* on the one hand or another anaerobic bacterium, and on the other hand *Methanobrevibacter smithii* or *Methanomassiliicoccus luminyensis*, or another methanogenic organism gives the possibility of providing a significant amount of methane.

The present invention therefore essentially consists in the biological production of methane (Biogas) by an association of a methanogenic bacterium and of an anaerobic bacterium being cultivated under aerobic conditions in a medium rich in antioxidant components and containing a hydrocarbon source.

To do this, the present invention provides a method for producing methane gas in a reactor by co-culture under an aerobic atmosphere, preferably of ambient air, of at least:
- a first microorganism consisting in an anaerobic bacterium able to produce hydrogen by fermentation in the presence of a substrate and/or a culture medium comprising or supplemented with carbohydrate(s), notably starch and/or sugars, and
- a second microorganism consisting in a methanogenic Archaea able to produce methane from hydrogen and from a substrate and/or culture medium comprising or supplemented with hydrocarbon compound(s), notably starch and/or sugars, and
- an organic and mineral substrate comprising components of culture media able to allow cultivation of both said first and second anaerobic microorganisms, said culture medium comprising or being supplemented with carbohydrate(s), notably starch and/or sugars, and further being supplemented with antioxidant compound(s).

More particularly, the other cultivation conditions, notably temperature, are suitable conditions for the cultivation of said microorganisms. In particular, the temperature has to be increased in order to incubate if necessary to a temperature promoting growth of said microorganisms, notably at least 30° C. or even 37° C.

It is understood that the method according to the present invention does not require the supply of external hydrogen and that the co-culture reactor comprises means for recovering the produced methane gas.

Preferably, the cultivation of said first microorganism is achieved first of all in said substrate and said second microorganism is introduced after said first microorganism has already produced fermentation products and hydrogen.

By "antioxidant compound", is meant here a compound with an antioxidant property, i.e. it reduces or prevents oxidation of other substances, notably in this case, other substances involved in the method of the invention under the conditions of the method according to the invention.

More particularly, said antioxidant compound is preferably selected from among ascorbic acid, uric acid and glutathione (γ-L-Glutamyl-L-cysteinylglycine). Ascorbic acid and uric acid are preferred since they are capable at specific doses of allowing cultivation at a higher oxygen level.

Still more particularly, said antioxidant compound is applied at a concentration of 1 µg/ml to 2 mg/ml, or in a molar concentration from $10^{-6}$ M to $10^{-2}$ M, preferably at least 1 g/l.

Preferably, said medium comprises a pH-regulating buffer substance for adjusting the pH from 7 to 7.5.

More particularly, said Archaea is an Archaea selected from the following Archae: *Methanobrevibacter, Methanosphaera, Methanomassiliicoccus, Methanobacterium, Methanococcus* and *Methanosaeta*.

More particularly, said Archaea is a Archaea selected from the following Archae: *Methanobrevibacter smithii, Methanobrevibacter orails; Methanosphaera stadtmanae, Methanomassiliicoccus luminyensis, Methanobacterium beijingense* and *Methanosaeta concilii*.

Still more particularly, said Archea is a *Methanobrevibactera smithii* or *Methanomassiliicoccus luminyensis*.

Strict anaerobic bacteria, i.e. they are not capable of being cultivated in the presence of oxygen or in concentrations of less than 1%, more commonly less than 0.1%, ideally 0%. From among strict anaerobic bacteria, more particularly mention is made of extracellular bacteria, i.e. bacteria which can only live on the exterior of cells.

More particularly, said anaerobic bacterium able to produce hydrogen is selected from bacteria from the Actinobacteria and Bacteroidetes families.

Preferably, said anaerobic bacterium is of the *Bacteroides* genus, these bacteria are in particular known for digesting starch while producing hydrogen.

More particularly, said anaerobic bacterium is *Bacteroides thetaiotaomicron*.

The bacteria *Lactococcus lactis* is also mentioned as an Actinobacteria.

More particularly, said culture medium comprises components which are found in the culture basis media able to cultivate an archaea or an anaerobic bacterium, comprising at least:

several carbon sources,
a phosphorus source, preferably a phosphate salt,
a source of nitrogen, preferably an ammonium salt,
at least one salt of metal selected from among K, Mg, Na, Ca, preferably NaCl.

More particularly, said culture medium is an acellular medium, is selected from among an axenic medium consisting of chemical or biological substances defined qualitatively and quantitatively, and an acellular medium comprising an extract of milled or lyzed material from pluricellular tissue.

More particularly, said culture medium is a conventional acellular medium of an anaerobic bacterium, preferably a medium comprising components selected from among an extract of pluricellular tissue milled material or lyzed material, an enzymatic digested material, notably an enzymatic digested material of casein, soy and/or animal tissue, a peptone, a yeast extract, a sugar such as dextrose or glucose, an NaCl and/or $Na_2PO_4$ salt.

Still more particularly, said culture medium is a conventional medium for cultivating anaerobic bacteria such as so called broth media of the heart-brain type, Columbia media with 5% of sheep blood or a Schaedler medium as described hereafter. Other suitable conventional media are the *Brucella* or Wilkins-Chagren media. Such acellular culture media are well known to one skilled in the art.

In particular it is possible to use polyvalent culture media for anaerobic microorganisms, notably Schaedler medium, said medium being supplemented with carbohydrate(s), preferably starch and sugar(s), and with antioxidant compound(s).

The inventors actually tested different molecules having an antioxidant activity and discovered that certain antioxidant compounds in certain concentrations have a greater effect on the growth of said bacteria.

Other features and advantages of the present invention will become better apparent upon reading the description which follows, made in an illustrative and non-limiting way, of an exemplary embodiment.

In order to illustrate the invention, the inventors cultivated methanogenic archaea notoriously recognized as strict anaerobic (recognized as being only cultivated in the strict absence of oxygen), in an aerobic atmosphere (i.e. open air, containing about 16% of oxygen) and in the presence of bacteria notoriously recognized as strict anaerobic bacteria, in bacterial and archae culture media notoriously recognized as anaerobic, said culture media being supplemented with anti-oxidant compounds for supporting growth in an ambient air atmosphere and supplemented with carbohydrate(s) for producing $H_2$ and $CH_4$.

1) Used Strains.

A methanogenic archaea *Methanobrevibacter smithii* of strain DSM 861 was obtained from the German collection of microorganisms and cell cultures (DSMZ, Braunschweig, Germany) also deposited at the ATCC under number ATCC 35061.

An archaea *Methanomassiliicoccus luminyensis* deposited at the deposit collection of microorganisms DSMZ (Germany), according to the Budapest Treaty, under number DSM 24529 was also tested as described in FR 124 779 (published under number 2 990 954).

Moreover, a strain of the anaerobic bacterium *Bacteroides thetaiotaomicron* was obtained through the <<culturomics>> study of the inventors (Lagier J C et al., Microbial culturomics: paradigm shift in the human gut microbiome study. Clin Microbiol Infect. 2012; 18:1185-93) also accessible in diverse deposit collections (CSUR P766 also deposited according to the Budapest Treaty at the deposit collection of micro-organisms DSMZ (Germany) on May 19, 2014 under the number of DSM 28808, other strains are also accessible in diverse deposit collections such as the strains DSM 2079, ATCC 29148 and NCTC 10582).

Another following anaerobic bacterium strain was also tested: *Lactococcus lactis* deposited according to the Budapest Treaty at the deposit collection of micro-organisms DSMZ (Germany) on May 19, 2014 under the number of DSM 28809, also available in diverse deposit collections including the National Collection of micro-organism cultures de CNCM 1-2716.

2) Aerobic Culture of Anaerobic Microorganisms by Means of Antioxidants.

For their production in a sufficient amount, both strains *M. smithii* or *M. luminyensis* and *B. thetaiotaomicron* were cultivated in an anaerobic atmosphere at 37° C. in a polyvalent culture medium. The Schaedler medium (Reference 42098; BioMérieux, La Balmes-les-Grottes, France) was also tested as well as the medium designated as <<SAB medium>> described in FR 124 779 (published under the number of 2 990 954) and WO 2013/0044933 customarily used for cultivating human methanogenic archaea and which seems to be suitable also for the cultivation of anaerobic bacteria.

The Schaedler medium (marketed by BioMérieux, Marcy l'étoile, France) had the following composition for 1 liter:

| | |
|---|---|
| Enzymatic digested material of casein | 5.6 g |
| Enzymatic digested material of soya cake | 1 g |
| Enzymatic digested material of animal tissue | 5 g |
| Yeast extract | 5 g |
| NaCl | 1.7 g |
| Potassium phosphate | 0.82 g |
| Dextrose | 5.82 g |
| Tris (hydroxymethyl) aminomethane | 3 g |
| Hemin | 0.01 g |
| L-cysteine | 0.4 g |

The SAB medium used was without any $Na_2S$ and of L-cysteine and comprised: $NiCl_2 \times 6H_2O$ (0.07 mg/l), $Na_2MoO_4 \times 2H_2O$ (0.02 mg/l), $FeSO_4 \times 7H_2O$ (0.2 mg/l), $MgSO_4 \times 7H_2O$ (0.01 g/l), $K_2HPO_4$ (0.5 g/l), $KH_2PO_4$ (0.5 g/l), KCl (0.05 g/l), $CaCl_2$ (0.05 g/l), NaCl (1.5 g/l), $NH_4Cl$ (1 g/l), Na-Acetate (1 g/l), yeast extract (1 g/l), Biotrypticase (1 g/l), Widdel trace amount solution (2 ml/l), Balch trace element solution (10 ml/l), Resazurin (1 mg/l), $Na_2Se_2O_3 \cdot 5H_2O$ (0.015 mg/l), $Na_2WO_4 \cdot 2H_2O$ (0.02 mg/l), $NiCl_2 \cdot 6H_2O$ (0.07 mg/l), $NaHCO_3$ (4 g/l), Na-Formate (0.4 g/l), Methanol (40 mM), Balch medium vitamin solution (10 ml/l), valeric acid (0.6 g/l), isovaleric acid (0.6 g/l), 2-methylbutyric acid (0.6 g/l), isobutyric acid (0.6 g/l), 2-methylvaleric acid (0.6 g/l).

The trace elements of Balch comprise NaCl, $FeSO_4$, $ZnSO_4$, $MgSO_4$, $MnSO_4$, $CoSO_4$, $H_3BO_3$, $NiCl_2$, $Na_2MoO_4$, $CaCl_2$.

The trace elements of Widdel comprise $FeCl_2$, $CoCl_2$, $MnCl_2$, $ZnCl_2$, $H_3BO_3$, $Na_2MoO_4$, $NiCl_2$ and $CuCl_2$.

The vitamins of the Balch medium comprise biotin, folic acid, pyridoxine hydrochloride, thiamine hydrochloride, riboflavin, nicotinic acid, DL-calcium pantothenate, vitamin B12, p-aminobenzoic acid and lipoic acid.

This Schaedler medium as well as this SAB medium were supplemented by adding carbohydrate(s) i.e. 1 g/L of rice starch and 1 g/L of glucose (Sigma-Aldrich, Saint-Quentin Fallavier, France) and addition of anti-oxidant compounds i.e. supplemented with the addition of 1 g/L of ascorbic acid (VWR International, Louvain, Belgium), 0.1 g/L of uric acid and 0.1 g/L of glutathione (Sigma-Aldrich, Saint-Quentin Fallavier, France).

The resazurin is applied as an indicator of oxidation-reduction at a concentration of 0.1 mg/mL for controlling the presence of oxygen (oxidized resazurin has a pink color and becomes transparent in the absence of oxygen).

The aerobic culture in ambient air of *M. smithii* or *M. luminyensis* and *B. thetaiotaomicron* was carried out in separate containers and in a same container incubated at 37° C. containing the culture medium supplemented with the addition of anti-oxidant compounds and carbon source compounds. The pH was adjusted to 7.5 by adding 10M KOH.

Both strains were cultivated separately as well as in a co-culture, under aerobic conditions and by inoculation of $10^5$ organism/mL of each strain with the culture medium supplemented according to the present invention and in parallel with the Schaedler or SAB medium supplemented with carbohydrates as mentioned above but, on the other hand without any anti-oxidant compounds.

The positive controls consist in a tube containing the supplemented culture medium above, inoculated under anaerobic conditions with $10^8$ microorganisms/L of *M. smithii* or *M. luminyensis* in the presence of a gas mixture of 80% $H_2$+20% of $CO_2$ at the pressure of two atmospheres required for optimum growth of the methanogenic archaea. The supplemented culture medium inoculated under anaerobic conditions with $10^8$ microorganisms/L of *M. smithii* or *M. luminyensis* without his gas mixture was introduced in order to check the growth of this methanogenic archaea without $H_2$. The culture medium supplemented by adding 1 g/L of rice starch and 1 g/L of glucose inoculated under anaerobic conditions with $10^8$ cells/L of *B. thetaiotaomicron* was introduced as a positive control and for checking the production of $H_2$ by *B. thetaiotaomicron* in an anaerobic culture. These controls were carried out in parallel in an ambient atmosphere (aerobic). The non-inoculated culture medium was introduced as a negative control.

3) Detection of the Growth by Gas Chromatography.

The growth of *M. smithii* or *M. luminyensis* was daily evaluated by the production of methane and the growth of *B. thetaiotaomicron* was daily evaluated by the production of hydrogen. The measurement of methane and of hydrogen was conducted by means of a gas chromatograph GC-8A (Shimadzu, Champs-sur-Marne, France) equipped with a heat conductivity detector and a Chromosorb WAW 80/100 meshes column SP100 (Alltech, Carquefou, France). The nitrogen $N_2$ at a pressure of 100 kPa was used as a carrier gas. The detector and the temperatures of the injector were 200° C. and the temperature of the column was 150° C.

4) Results.

4.1) Controls.

The negative controls remain negative without any growth occurring after one week of incubation indicating that the results reported here are not simply the result of a contamination by other microorganisms.

The positive controls were positive with production of methane observed in the anaerobic culture of *M. stmithii* or *M. luminyensis* and with a production of hydrogen observed in the anaerobic culture of *B. thetaiotaomicron*. There was no detectable production of methane in the culture of *M. smithii* or *M. luminyensis* inoculated alone under anaerobic conditions and under aerobic conditions without any gas mixture. Also, the culture of *B. thetaiotaomicron* inoculated under aerobic conditions without any antioxidant compounds remained negative and hydrogen was not produced.

4.2) Aerobic Co-culture.

After incubation for 24 hours at 37° C. in ambient air (under aerobic conditions), a culture medium without any anti-oxidant compounds retained its pink color indicating the presence of oxygen. The aerobic culture medium with the anti-oxidant compounds became transparent indicating the absence of oxygen after its reduction by the antioxidant compounds.

The culture medium inoculated under aerobic conditions with *M. smithii* or *M. luminyensis* with the anti-oxidant compounds became transparent, but the culture remained negative and methane was not produced. The culture medium inoculated under aerobic conditions with *B. thetaiotaomicron* in the presence of the antioxidants became transparent and bacterial growth was observed with production of hydrogen.

The co-cultures of *M. smithii* or *M. luminyensis* and *B. thetaiotaomicron* achieved under aerobic conditions with anti-oxidant compounds all gave a positive culture for *B. thetaiotaomicron* with production of hydrogen after 24 hour incubation. On the other hand, in certain experiments, no growth was observed for *M. smithii* or *M. luminyensis* (although the culture medium became transparent). The inventors made the assumption that *M. smithii* or *M. luminyensis* were dead because of their exposure to oxygen before the medium was reduced by the anti-oxidant compounds.

Experiments were conducted with the introduction of *B. thetaiotaomicron* at t0 and *M. smithii* or *M. luminyensis* added at t0+24 hours of incubation. The addition of *M. smithii* or *M. luminyensis* after 24 hours of incubation in every case gave the possibility of re-establishing its growth by consumption of the hydrogen produced beforehand by *B. thetaiotaomicron* in the presence of antioxidant compounds and by avoiding mortal exposure to oxygen.

This same experiment was conducted without any anti-oxidant compound and the culture remained negative for both of the tested strains.

On the other hand, the anaerobic bacterium *Lactococcus lactis* DSM 28809 was also successfully tested combined with both of these archaea.

4.3) Interpretation

These results indicate that it is possible to cultivate in ambient air (aerobic condition) bacteria notoriously recognized as strictly anaerobic, in a suitable medium containing a suitable mixture of antioxidants.

Under these conditions, the anaerobic bacteria produce hydrogen which may then be used in a second phase by the methanogenic archaea for producing methane.

It is shown that it is possible to produce methane in ambient air, under suitable conditions of co-culture of bacteria and of anaerobic methanogens in a culture medium supplemented with carbon source compounds and antioxidant compounds.

The introduction of the methanogenic archaea in a medium already containing fermentation products and hydrogen is preferable.

The invention claimed is:

1. A method for producing methane gas, the method comprising:
   co-culturing, in a reactor under an aerobic atmosphere, at least:
   a first microorganism that is an anaerobic bacterium belonging to a Bacteroidetes family, or an Actinobacteria family, said first microorganism being able to produce hydrogen by fermentation in the presence of at least one of a substrate and a culture medium comprising, or supplemented with, a carbohydrate, and
   a second microorganism that is a methanogenic Archaea genus selected from the group consisting of *Methanobrevibacter, Methanosphaera, Methanomassiliicoccus, Methanobacterium, Methanococcus*, and *Methanosaeta*, said second microorganism being able to produce methane from hydrogen and from at least one of a substrate and a culture medium comprising, or supplemented with, a carbohydrate, and
   an organic and mineral substrate comprising components of culture media able to allow the cultivation of both said first and said second microorganisms, said culture medium comprising, or being supplemented with, a carbohydrate and further being supplemented with an antioxidant compound;
   wherein said antioxidant compound is at least one of ascorbic acid and uric acid.

2. The method according to claim 1, wherein the cultivation of said first microorganism is first carried out in said substrate, and said second microorganism is introduced after said first microorganism has produced fermentation products and hydrogen.

3. The method according to claim 1, wherein said antioxidant compound comprises at least both ascorbic acid and uric acid.

4. The method according to claim 1, wherein said second microorganism is selected from the group consisting of *Methanobrevibacter smithii, Methanobrevibacter oralis, Methanosphaera stadtmanae, Methanomassiliicoccus luminyensis, Methanobacterium beijingense*, and *Methanosaeta concilii*.

5. The method according to claim 1, wherein said second microorganism is *Methanobrevibacter smithii*, or *Methanomassiliicoccus luminyensis*.

6. The method according to claim 1, wherein said first microorgansism is a *Bacteroides* genus.

7. The method according to claim 1, wherein said first microorganism is *Bacteroides thetaiotaomicron*, or *Lactococcus lactis*.

8. The method according to claim 1, wherein said first microorganism is *Lactococcus lactis*.

9. The method according to claim 1, wherein said second microorganism is Methanobrevibacter smithii DSM 861 or *Methanomassiliicoccus luminyensis* DSM 24529, and the first microorganism is *Bacteroides thetaiotaomicron* DSM 28808, or *Lactococcus lactis* DSM 28809.

10. The method according to claim 1, wherein said culture medium comprises:
    a plurality of carbon sources,
    a phosphorus source,
    a nitrogen source, and
    at least one salt of a metal selected from the group consisting of K, Mg, Na, and Ca.

11. The method according to claim 1, wherein said antioxidant compound is added at a concentration of from 1 mg/l to 2 g/l.

12. The method according to claim 1, wherein said culture medium comprises a pH-regulating buffer substance for adjusting the pH from 7 to 7.5.

13. The method according to claim 1, wherein said culture medium comprises components of Schaedler's medium supplemented with a carbohydrate and a sugar, and with said antioxidant compound.

14. The method according to claim 1, wherein the aerobic atmosphere is ambient air.

15. The method according to claim 1, wherein said first microorganism is *Bacteroides thetaiotaomicron* or *Lactococcus lactis*, and said second microorganism is *Methanobrevibacter smithii* or *Methanomassiliicoccus luminyensis*.

16. The method according to claim 3, wherein said antioxidant compound further comprises glutathione.

17. The method according to claim 1, wherein said antioxidant compound further comprises glutathione.

* * * * *